US006944985B2

(12) United States Patent
Fishman

(10) Patent No.: US 6,944,985 B2
(45) Date of Patent: Sep. 20, 2005

(54) IDENTIFICATION BRACELET

(76) Inventor: Marie T. Fishman, 2551 E. Brentwood Dr., Salt Lake City, UT (US) 84121

(*) Notice: Subject to any disclaimer, the term of this patent is extended or adjusted under 35 U.S.C. 154(b) by 0 days.

(21) Appl. No.: 10/617,216

(22) Filed: Jul. 8, 2003

(65) Prior Publication Data

US 2005/0005491 A1 Jan. 13, 2005

(51) Int. Cl.[7] ............................ A61B 5/117; A44C 5/14
(52) U.S. Cl. .......................................... 40/633; 224/169
(58) Field of Search ................... 40/633; 224/164–179; 368/281, 282; 24/713; 63/21; D10/30, 32

(56) References Cited

U.S. PATENT DOCUMENTS 2,073,280 A * 3/1937 Lederer ....................... 40/633
3,330,057 A * 7/1967 Rodgers ...................... 40/633
3,526,985 A * 9/1970 Rieth .......................... 40/117
3,645,023 A * 2/1972 Larson ........................ 40/633
3,810,566 A * 5/1974 Adams et al. ................ 40/709
4,199,882 A 4/1980 Clayman
4,226,036 A 10/1980 Krug
D316,983 S * 5/1991 Houlihan ..................... D10/39
5,283,969 A 2/1994 Weiss
5,493,805 A 2/1996 Penuela et al.
5,499,468 A 3/1996 Henry
5,577,007 A * 11/1996 Houlihan .................... 368/282
5,649,381 A 7/1997 Studer
5,765,875 A 6/1998 Rowley
6,085,449 A * 7/2000 Tsui ............................. 40/1.6
6,186,552 B1 * 2/2001 Seabrook ..................... 281/45
6,510,988 B1 1/2003 Kraus

* cited by examiner

*Primary Examiner*—Andrew D. Wright
(74) *Attorney, Agent, or Firm*—Thorpe North & Western LLP

(57) ABSTRACT

An information bracelet for protectively storing information related to an individual wearing the bracelet includes a bracelet body having a cavity defined therein. The cavity can be configured to store and protect an information-bearing medium on which the information related to the individual can be disposed. A strap assembly can also be provided and includes a strap member and a pair of clasps. The pair of clasps can be coupled to opposite ends of the strap member and can be directly coupleable to opposite ends of the bracelet body. The clasps can be configured to facilitate removable coupling of the strap assembly to the bracelet body.

41 Claims, 5 Drawing Sheets

IDENTIFICATION BRACELET

BACKGROUND OF THE INVENTION

1. Field of the Invention

The present invention relates generally to a bracelet for storing information relating to a wearer of the bracelet.

2. Related Art

It is often the case that it is desirable to include information on a person relating to that person. For instance, small children are often unable to remember information such as their address, telephone number, etc., that may be necessary for third parties to ascertain in the event of some problem. This can be problematic if a young child becomes lost and may be unable to provide accurate identification information to people such as police who are attempting to locate the parents or caretaker of the child. This problem can be further exacerbated when the child is involved in a stressful situation, such as suffering an injury or being involved in accident, in which case even children normally capable of recalling and providing such information may be unable to do so.

Similar problems are also shared by aging adults or those with medical problems. For instance, it is recommended that people of all ages with certain medical conditions include information on their person identifying the medical condition. In this manner, emergency or medical personnel can be made aware of such information and treat the individual accordingly. In addition, active adolescents and adults often participate in outdoor and recreational activities in which carriage of wallets, purses, etc., is not convenient. In the event that such individuals become injured, it can be difficult, if not impossible, for emergency personnel to identify the individual and/or ascertain who should be contacted to report the injury, i.e., the individual's parents, spouse, etc.

For these reasons, persons with medical conditions, caretakers of children or older adults, and active adolescents and adults (collectively referred to as "individuals") often wish to provide information relating to the individual in a manner that can be accessed by third parties in the event that the individual is unable to provide the information themselves. This can most effectively be done by providing and storing the information on the person of the individual.

Providing information relating to an individual on the person of the individual can be done in a number of ways. For instance, the individual can be provided with a card or other paper on which the information is written and the card or paper can be stored in the individual's pocket or purse. While this information may be useful by third parties in the event that it becomes necessary, third parties may have no knowledge of the existence of such a paper and may not think to search for something of the kind.

In addition, the individual may not know of or be able to understand the importance of such a card or paper and may discard or otherwise lose the paper. For these reasons, devices such as "medical alert" jewelry have been developed on or in which such information can be disposed. If the individual wearing such a device continues to wear the device, and in the event that such a device can store sufficient information to be of use, these conventional methods of identification provide some limited benefits.

However, conventional identification devices have proved problematic in a number of ways. For instance, many individuals who are provided and/or instructed to wear such devices resist doing so and may remove the device when unattended. This can be especially the case with young children, who may not wish to wear a device that other children are not wearing or that, in the child's opinion, is not "cool," or attractive enough to warrant continued use, or that is uncomfortable or overly heavy to wear. Also, conventional "medical alert" jewelry has proved to be limited in the amount and current status of information that can be displayed. For instance, many conventional jewelry identification devices are engraved with information, which results in a limited amount of information being recordable on the device. In addition, once engraved on the device, it is difficult, if not impossible, to update the information to maintain a current status of the information.

For at least these reasons, conventional identification devices are not particularly suited for storing complete identification information, such as addresses, telephone numbers, caretaker names and contact information, etc. Such devices are often limited to providing only a limited, basic amount of information, and not detailed information such as third party contact information, office contact information, etc. Furthermore, even if conventional identification devices can be provided with a desired amount of information, many people are reluctant to wear such devices as they may appear unattractive or out of step with current trends, or may be uncomfortable, heavy, or bulky to wear.

SUMMARY OF THE INVENTION

It has been recognized that it would be advantageous to develop a device that enables information relating to an individual to be protectively stored upon the person of the individual. The invention provides an information bracelet for protectively storing information related to an individual wearing the bracelet, and includes a bracelet body having a cavity defined therein. The cavity can be configured to store and protect an information-bearing medium on which the information related to the individual can be disposed. A strap assembly can also be provided and includes a strap member and a pair of clasps. The pair of clasps can be coupled to opposite ends of the strap member and can be directly coupleable to opposite ends of the bracelet body. The clasps can be configured to facilitate removable coupling of the strap assembly to the bracelet body.

In accordance with another aspect of the present invention, an information bracelet for protectively storing information related to an individual wearing the bracelet is provided, and includes a bracelet body having a cavity defined therein. The cavity can be configured to store and protect an information-bearing medium on which the information related to the individual can be disposed. A strap assembly is also provided and can include a strap member and a clasp. The clasp can have a pair of splayable fingers, each finger including at least one receiving aperture configured to receive at least a portion of the bracelet body to removably couple the strap assembly to the bracelet body.

In accordance with another aspect of the present invention, an information bracelet for protectively storing information related to an individual wearing the bracelet is provided, and includes a bracelet body having a cavity defined therein. The cavity can be configured to receive, store and protect an information-bearing medium on which the information related to the individual can be disposed. The body can include a lower and an upper section, the lower and upper sections being engageable with each other to thereby cooperatively define the cavity in the bracelet body for receiving the information-bearing medium. The lower section can include a protruding lower retention arm, and the upper section can include a protruding upper retention arm. The lower and upper retention arms can each be sized and shaped to cooperatively form a body retention arm when the lower and upper sections are engaged with each other. A strap assembly can also be included and can include a strap member and a clasp, coupled to the strap member and removably coupled to the body retention arm, to both couple the body to the strap assembly and to secure the lower and upper sections of the body in engagement with each other.

In accordance with yet another aspect of the invention, a method for storing information related to an individual in a bracelet wearable by the individual is provided, and includes the steps of: a) providing a substantially water-resistant information-bearing medium on which the information related to the individual can be disposed; b) storing the information-bearing medium within a cavity of the bracelet defined between a lower and an upper section of a bracelet body; c) engaging the lower and upper sections with each other; and d) clasping a protruding portion of both the lower and upper sections with a clasp coupled to a bracelet strap.

Additional features and advantages of the invention will be apparent from the detailed description which follows, taken in conjunction with the accompanying drawings, which together illustrate, by way of example, features of the invention.

DETAILED DESCRIPTION

Figure 1:
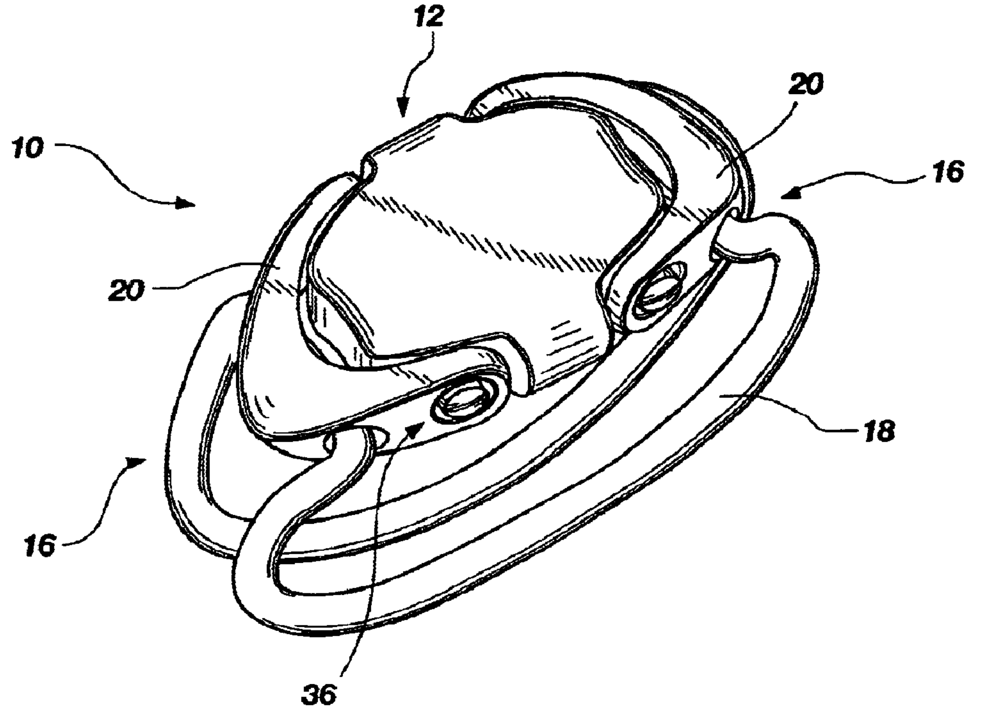
FIG. 1 is a perspective view of an identification bracelet in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in FIG. 1, an identification bracelet, indicated generally at 10 is provided in accordance with one aspect of the present invention. The information bracelet can include a bracelet body 12 which has a cavity (14 in FIG. 2) defined therein. The cavity can be configured to store and protect an information-bearing medium (shown by example in FIG. 5) on which the information related to the individual can be disposed. A strap assembly 16 can also be provided and can include a strap member 18, and a pair of clasps 20. The clasps can be coupled to opposite ends of the strap member and are directly coupleable to opposite ends of the bracelet body. The clasps are thereby configured to facilitate removable coupling of the strap assembly to the bracelet body.

The identification bracelet can be utilized by a variety of individuals in various situations. For example, the bracelet can be provided to young children with information relating to the child disposed on the information-bearing medium stored in the cavity of the bracelet. The information relating to the child can then be easily accessed by police, emergency personnel, or other third parties in the event the child becomes lost or is injured. As used herein, the term "information relating to an individual" is meant to include a variety of information related to an individual, including, without limitation: identification information, such as name, address, home telephone number, office telephone number, cellular telephone number, etc.; health information, such as current or past medical conditions; medication information, including current medications which the individual is taking and allergies to other medications and foods; scheduling information, such as appointments the individual must keep or addresses at which the appointment must be kept; and third party contact information, such as names, telephone numbers and addresses of parent, spouse, guardian or caretaker, school or institution with which the individual is associated, etc.

The present invention thus allows substantially all pertinent information relating to the child to be protectively stored upon the person of the child. While beneficial for children, the present invention is not limited to use by young children, but can be used by a variety of individuals, including adults. The bracelet can be advantageously used by aging adults, who may have difficulty remembering particular information, or by those with medical conditions that should be made known to emergency personnel and others. Also, active adults or adolescents participating in sporting events, such as bicycling, jogging, etc., can benefit from use of the bracelet, as they may not wish to carry extraneous objects such as wallets and purses when jogging or biking, but would like to carry their personal information for emergency purposes.

Figure 2:
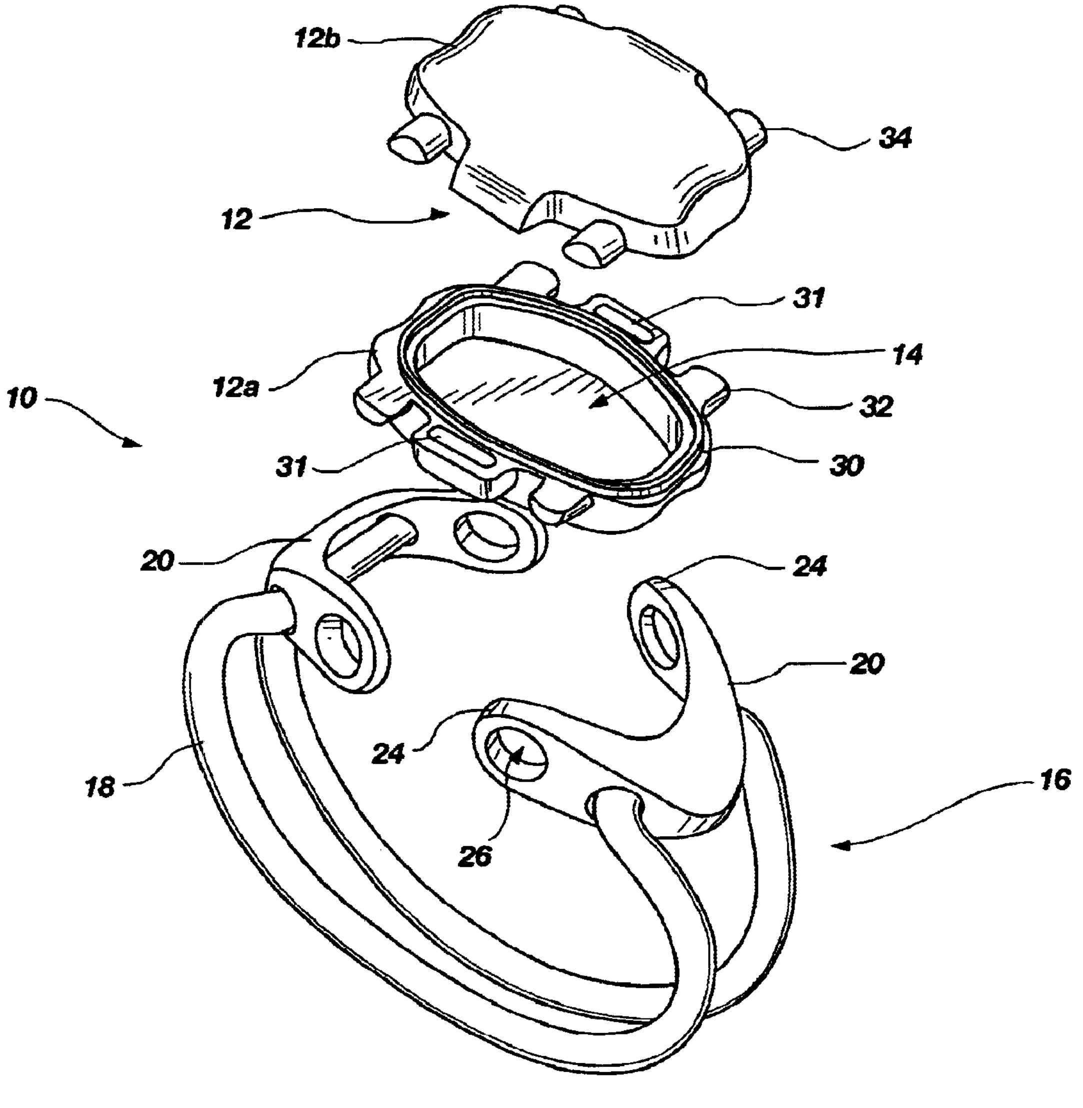
FIG. 2 is an exploded, perspective view of the identification bracelet of FIG. 1.

The various components of one embodiment of the invention are shown in an exploded view in FIG. 2. In this embodiment, the clasps 20 can each include a pair of splayable fingers 24 which can be splayed, or spread apart, to receive the bracelet body 12 and to secure the strap assembly to the bracelet body. In this aspect, each splayable finger can include at least one receiving aperture 26 that can be configured to receive a portion of the bracelet body to removably couple the clasp to the bracelet body. Thus, to secure the strap assembly to the bracelet body, each of the fingers 24 can be splayed and the clasp can be disposed over a portion of the bracelet body. Once properly positioned, the fingers can be released from their splayed configuration, at which point they will return to their original configuration and securely grasp the bracelet body.

To enable the strap assembly 16 to be easily attached to and removed from the bracelet body 12, the fingers 24 of the claps 20 can each be formed of a resilient material having plastic memory. Thus, as the fingers are splayed or otherwise opened for engagement over the bracelet body, the fingers will return to their original position due to the memory of the plastic material. As used herein, the term "plastic" is understood to refer to an elastic property of the material, and not necessarily to material commonly referred to as "plastic," i.e., polymer materials in general.

As also illustrated in FIG. 2, the bracelet body 12 can include a lower 12*a* and upper 12*b* section which can be engaged together to thereby cooperatively form the cavity 14. The lower and upper sections can each include a recessed portion which collectively define the cavity. Alternately, only one or the other lower and upper sections can include a recessed portion that becomes a closed cavity upon mating with the other section. A seal 30 can be included on or in either or both of the upper and lower sections to provide a substantially water-resistant seal around at least a portion of the cavity. In this manner, in the event that the individual wearing the bracelet exposes the bracelet to a wet environment, the information disposed on the information-bearing medium can be protected from exposure to water and other contaminants.

The seal 30 can be of a number of configurations, as known in the relevant art, including an o-ring disposed in a channel, etc. Also, latch mechanisms 31 can be included in either or both the lower 12*a* and upper 12*b* sections of the body 12 to aid in securing the sections to each other and about the seal. The latch mechanism can be "snapped" closed and pried open by inserting a coin or fingernail between the sections.

The lower 12*a* section of the bracelet body 12 can include a protruding lower retention arm 32 and the upper 12*b* section of the bracelet body 12 can include a protruding upper retention arm 34. The lower and upper retention arms can be sized and shaped to cooperatively form a body retention arm (36 in FIGS. 1 and 3B) when the upper and lower sections are engaged with each other. The receiving aperture 26 of the clasps 20 can receive and secure the body retention arm therein. In this manner, the clasps not only secure the bracelet body 12 to the strap assembly 16, but the clasps also secure the upper and lower body sections in engagement with each other.

Figure 3A:
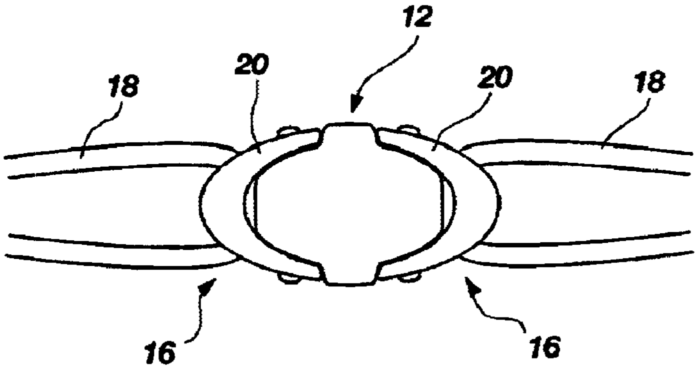
FIG. 3A is a top view of an identification bracelet in accordance with one aspect of the present invention.
Figure 3B:
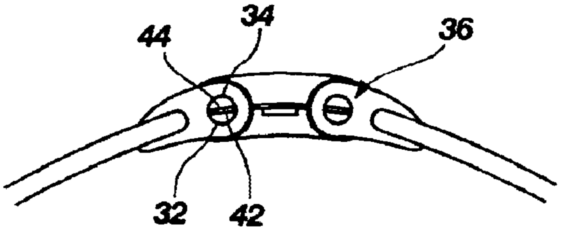
FIG. 3B is a side view of the identification bracelet of FIG. 3A.

As shown in side view in FIG. 3B, the protruding lower retention arm 32 can include an upper mating surface 42 and the upper retention arm 34 can include a lower mating surface 44. The upper and lower mating surfaces can include substantially matching contours which can enable a snug fit between the two retention arms. As used herein, the term "substantially matching contours" is understood to mean contours which complement, or are counter-parts of each other. Thus, in one embodiment, the substantially matching contours are substantially planar, as shown in FIG. 3B. In other embodiments, the contours can include undulating or angled contours that complement each other, as would occur to one skilled in the relevant art. In the embodiment shown, the upper and lower retention arms each have a substantially half-circular cross-section and collectively form a body retention arm having a substantially circular cross-section.

In one aspect of the invention, shown in FIG. 3A, the splayable fingers of the clasps define a substantially elliptical receiving area in which the bracelet body is received by the clasps. The elliptical receiving area can provide an aesthetically pleasing visual appearance while maximizing the securing force applied by the clasps to the bracelet body. As will be appreciated from viewing FIG. 3A, the bracelet provides an easily-identifiable and aesthetically pleasing appearance. It is believed that law enforcement and emergency personnel can be educated to recognize the appearance of the bracelet and immediately associate the bracelet as a source of information relating to the individual wearing the bracelet.

Figure 3C:
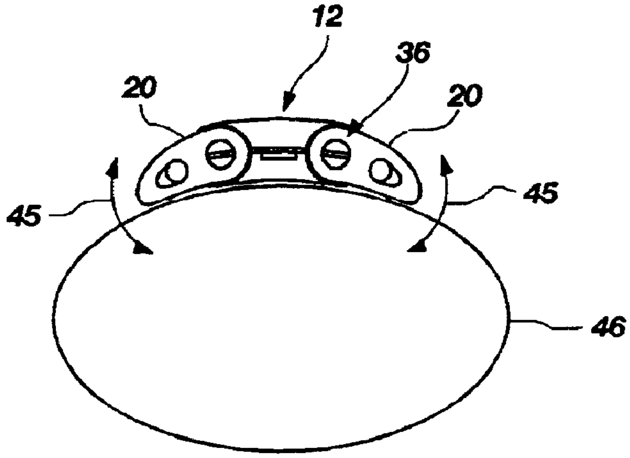
FIG. 3C is a partial side view of the identification bracelet of FIG. 3A.

As shown in FIG. 3C, the clasps 20 can be rotatably coupled to the bracelet body 12 to facilitate rotation or hinging of the clasps about ends of the bracelet body, as indicated by arrows 45. In this manner, the clasps can adjust to varying sized and shaped wrists (shown in cross section at 46) of wearers of the bracelet, to provide a more secure, comfortable fit on the wearer's wrist. The substantially circular cross-section of the body retention arms 36 can aid in the rotatable coupling of the clasps.

The strap member 18 shown in FIGS. 1 through 3B includes a generally tubular or cylindrical strap member coupled to a pair of clasps 20. The cylindrical strap is sufficiently strong to safely secure the bracelet to a wearer's wrist, yet provides an aesthetically pleasing appearance and comfortable fit on the wearer's arm. As the strap assembly 16 can be easily and fully removed from the body 12 of the bracelet, the present invention provides an identification bracelet that can be supplied with interchangeable strap assemblies. The strap member, clasps and bracelet body can be formed of a variety of materials exhibiting a variety of colors and appearances.

For instance, to provide a more interesting and fashionable bracelet, the components of the bracelet can be made of different colors, and can be interchanged to allow a user to change the bracelet's appearance from one day to the next. This feature can be especially appealing to children, who may as a result view the bracelet as more of an interesting object to wear, and may not be as likely to resist the "requirement" that the bracelet be worn. Also, the colors of the bracelet can be tailored to make the bracelet more appealing to children by selecting a child's favorite color, the colors of the child's school or club, favorite sports team, etc.

Figure 4A:
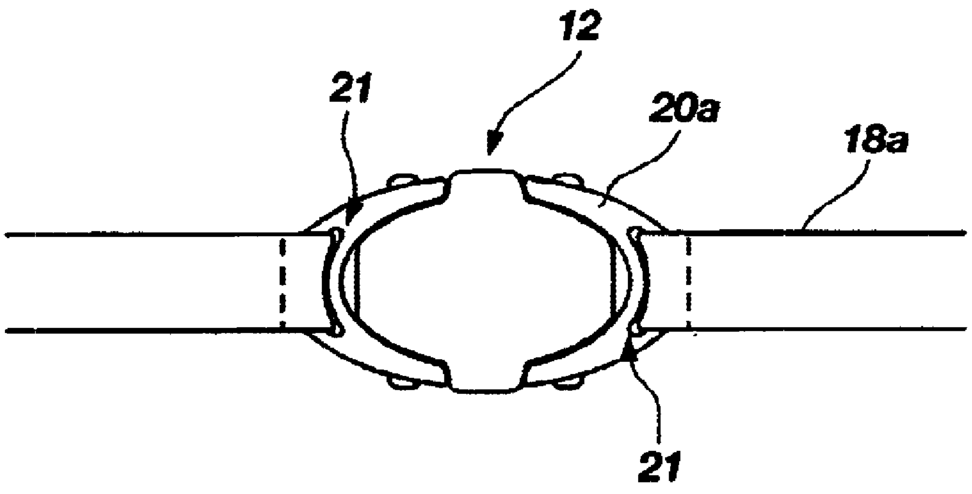
FIG. 4A is a top view of an identification bracelet in accordance with another aspect of the present invention.
Figure 4B:
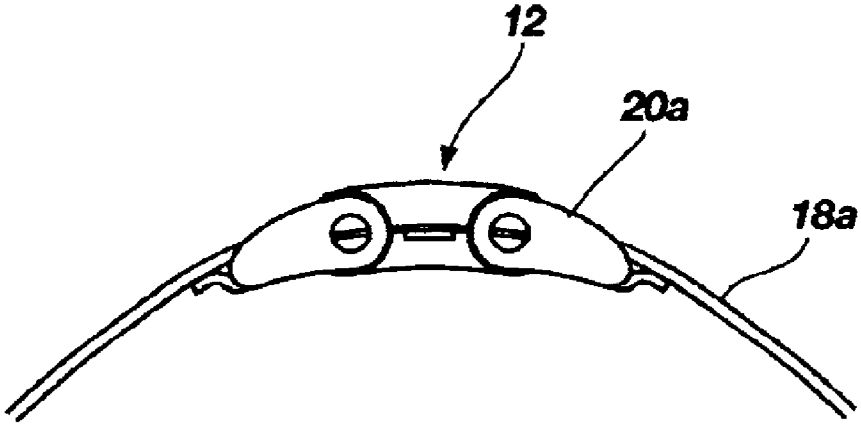
FIG. 4B is a side view of the identification bracelet of FIG. 4A.

As shown in FIGS. 4A and 4B, the strap member 18*a* can be of a variety of types, including a generally flat configuration, similar to a band of a wristwatch. In this aspect, the strap may include buckles, hook-and-loop fasteners or other attachment means (not shown) to enable the strap to be attached to and adjusted for a particular wearer. The clasps 20*a* of this embodiment can be configured to be adaptable to the generally flat strap member. For instance, elongate slots 21 can be included in the clasps to receive and secure the strap member. The clasps can include multiple holes or slots to accommodate a number of strap configurations with individual clasps. Also, while the embodiments illustrated in the figures include a strap member that is fixedly attached to the clasps, the bracelet can include clasps and strap members that can be removably coupled to each other. In addition, the strap member can be formed of an elastic material that can expand to allow an individual's hand to pass through the strap, and contract upon the individual's wrist to secure the bracelet to the individual.

Figure 5:
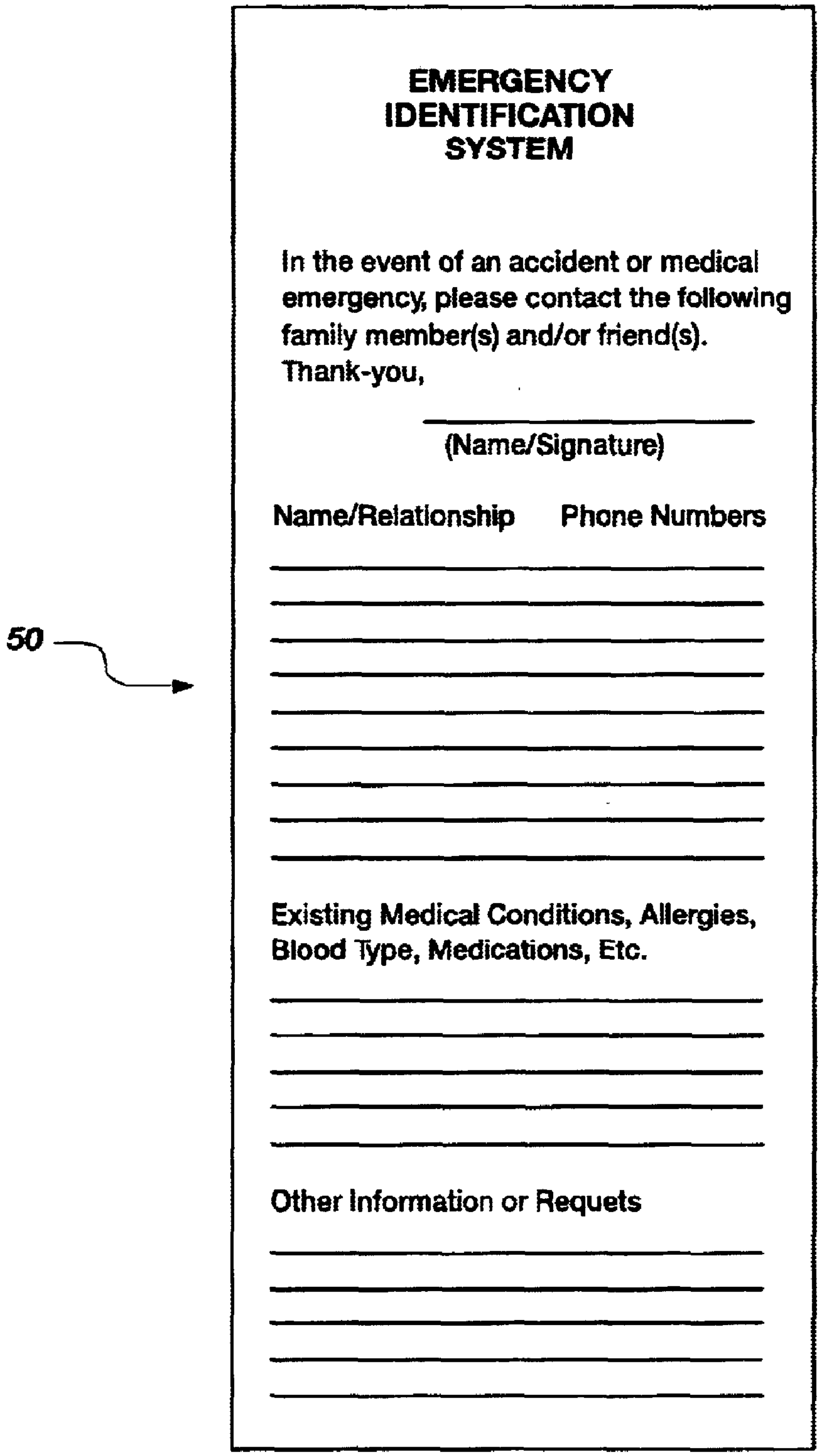
FIG. 5 is a schematic view of an information-bearing medium in accordance with one aspect of the invention.

One example of an information-bearing medium 50 in accordance with the invention is illustrated in FIG. 5. The medium can be formed of a variety of materials and can include any device or object on which information can be disposed. The medium can be formed of paper, fabric, polymer materials, and specialized materials such as the material known as Tyvek®. In one aspect of the invention, the information-bearing medium can be substantially water resistant to ensure that the information related to the child or individual is not inadvertently washed or erased from the information-bearing medium. As used herein, the term "substantially water resistant" is understood to mean a condition in which the medium or device is not penetrated by moisture under normal atmospheric conditions.

As illustrated, the information-bearing medium 50 can include space for a variety of information to be disposed on the medium. In addition, as the medium is not dedicated to a "set" group of data, the information related to the individual can be updated to reflect current events. For instance, if the individual begins a new medication regiment, the medication information can be updated or changed. Similarly, if a child is left with a new, temporary daycare provider, the new information can be quickly added to the medium by the child's parent or guardian. Also, if a child is to participate in a "field-trip" or other activity for the day, temporary contact information can be added to the list, such as the name of a teacher or counselor in charge of the trip, transportation information, etc. In the event a family is on vacation and staying at a particular hotel, the name and contact information for the hotel can be added to the medium.

The information-bearing medium can disposed in the cavity 14 in a number of manners, and can be rolled, folded, accordion-folded, etc., to provide a medium that can be large enough to contain a great deal of information but can be folded or rolled into a sufficiently small size to fit within the cavity. The medium can be sized and shaped in a variety of manners, and in one aspect, the medium can include a strip of material formed of sections sized and shaped to conform to an interior shape of the cavity in which the medium is disposed. In this manner, the sections can be folded on top of each other to form a compact, folded medium shaped like the cavity that utilizes substantially all of the space in the cavity. In addition, adhesive can be provided on the medium to ensure that at least a portion of the medium is adhered to the body so that the medium will not become detached from the body.

In addition, a plurality of media can be supplied with each bracelet to allow a new medium to be used in the event the original medium becomes lost, worn or depleted of usable space on which information relating to the individual can be written or disposed. In addition, one or more substantially "blank" information-bearing media can be supplied with each bracelet to allow a user or owner of the bracelet to further customize the type of information disposed on the media.

In accordance with another aspect of the invention, a method for storing information related to an individual in a bracelet wearable by the individual is provided, and can include the steps of: providing a substantially water-resistant information-bearing medium on which the information related to the individual can be disposed; storing the information-bearing medium within a cavity of the bracelet defined between a lower and an upper section of a bracelet body; engaging the lower and upper sections with each other; and clasping a protruding portion of both the lower and upper sections with a clasp coupled to a bracelet strap.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. An information bracelet for protectively storing information related to an individual wearing the bracelet, comprising:

a bracelet body having a cavity defined therein, the cavity storing and protecting therein an information-bearing medium on which the information related to the individual can be disposed, the body including a lower and an upper section, the lower and upper sections being engageable with each other to thereby cooperatively define the cavity for receiving the information-bearing medium;

the lower section of the body including a protruding lower retention arm, and the upper section of the body including a protruding upper retention arm, the lower and upper retention arms each being sized and shaped to cooperatively form a body retention arm when the lower and upper sections are engaged with each other; and a strap assembly, including;

a strap member; and a pair of clasps, coupled to opposite ends of the strap member and directly coupleable to opposite ends of the bracelet body, the clasps being configured to facilitate removable coupling of the strap assembly to the bracelet body.

2. The bracelet of claim 1, wherein the clasps are rotatably coupled to the bracelet body to facilitate rotation of the clasps relative to the body to allow the bracelet to conform to a shape of a wrist of the individual wearing the bracelet.

3. The bracelet of claim 1, wherein the clasps each include a pair of splayable fingers, each finger including at least one receiving aperture configured to receive a portion of the bracelet body to removably couple the clasps to the bracelet body.

4. The bracelet of claim 1, wherein the clasps each include a pair of splayable fingers formed of a material having plastic memory.

5. The bracelet of claim 1, wherein at least one of the lower and upper sections includes a seal, configured to provide a substantially water-resistant seal around at least a portion of a perimeter of the cavity.

6. The bracelet of claim 1, wherein the lower section includes a protruding lower retention arm having an upper mating surface, and wherein the upper section includes a protruding upper retention arm having a lower mating surface, the lower and upper mating surfaces having substantially matching contours and being configured to cooperatively form a body retention arm when the lower and upper sections are engaged with each other.

7. The bracelet of claim 6, wherein the lower and upper mating surfaces are substantially planar.

8. The bracelet of claim 7, wherein the lower retention arm and the upper retention arm each have a substantially half-circular cross section, and wherein the lower and upper retention arms cooperatively form a body retention arm having a substantially circular cross section.

9. The bracelet of claim 1, wherein the clasps each include a pair of splayable fingers, the splayable fingers defining a substantially elliptical receiving area in which the body is received by the clasp.

10. The bracelet of claim 1, wherein the information-bearing medium is substantially water resistant.

11. The bracelet of claim 1, wherein the information related to the individual includes information selected from the group consisting of: identification information; health information; medication information; scheduling information; and third party contact information.

12. An information bracelet for protectively storing information related to an individual wearing the bracelet, comprising:

a bracelet body including a lower and an upper section, the lower and upper sections being engageable with each other to thereby cooperatively define a cavity in the bracelet body, the cavity being configured to store and protect an information-bearing medium on which the information related to the individual can be disposed;

the lower section including a protruding lower retention arm, and the upper section including a protruding upper retention arm, the lower and upper retention arms each being sized and shaped to cooperatively form a body retention arm when the lower and upper sections are engaged with each other;

a strap assembly, including;

a strap member; and a pair of clasps, coupled to opposite ends of the strap member and directly coupleable to opposite ends of the bracelet body, the clasps being configured to facilitate removable coupling of the strap assembly to the bracelet body; and wherein the clasps each include a receiving aperture configured to receive and secure the body retention arm to both couple the body to the strap assembly and to secure the lower and upper sections of the body in engagement with each other.

13. An information bracelet for protectively storing information related to an individual wearing the bracelet, comprising:

a bracelet body having a cavity defined therein, the cavity storing and protecting therein an information-bearing medium on which the information related to the individual can be disposed; and a strap assembly, including;

a strap member; and a clasp, having a pair of splayable fingers, each finger including at least one receiving aperture configured to receive at least a portion of the bracelet body to removably couple the strap assembly to the bracelet body.

14. The bracelet of claim 13, wherein the fingers are rotatably coupled to the bracelet body to facilitate rotation of the clasps relative to the body to allow the bracelet to conform to a shape of a wrist of the individual wearing the bracelet.

15. The bracelet of claim 13, wherein the splayable fingers are formed of a material having plastic memory.

16. The bracelet of claim 13, wherein the body includes a lower and an upper section, the lower and upper sections being engageable with each other to thereby cooperatively define the cavity in the bracelet body for receiving the information-bearing medium.

17. The bracelet of claim 16, wherein at least one of the lower and upper sections includes a seal, configured to provide a substantially water-resistant seal around at least a portion of a perimeter of the cavity.

18. The bracelet of claim 16, wherein the lower section includes a protruding lower retention arm, and wherein the upper section includes a protruding upper retention arm, the lower and upper retention arms each being sized and shaped to cooperatively form a body retention arm when the lower and upper sections are engaged with each other.

19. The bracelet of claim 16, wherein the lower section includes a protruding lower retention arm having an upper mating surface, and wherein the upper section includes a protruding upper retention arm having a lower mating surface, the lower and upper mating surfaces having substantially matching contours and being configured to cooperatively form a body retention arm when the lower and upper sections are engaged with each other.

20. The bracelet of claim 19, wherein the lower and upper mating surfaces are substantially planar.

21. The bracelet of claim 20, wherein the lower retention arm and the upper retention arm each have a substantially half-circular cross section, and wherein the lower and upper retention arms cooperatively form a body retention arm having a substantially circular cross section.

22. The bracelet of claim 13, wherein the splayable fingers define a substantially elliptical receiving area in which the body is received by the clasp.

23. The bracelet of claim 13, wherein the information-bearing medium is substantially water resistant.

24. The bracelet of claim 13, wherein the information related to the individual includes information selected from the group consisting of: identification information; health information; medication information; scheduling information; and third party contact information.

25. An information bracelet for protectively storing information related to an individual wearing the bracelet, comprising:

a bracelet body having a cavity defined therein, the cavity storing and protecting therein an information-bearing medium on which the information related to the individual is disposed; and a strap assembly, including;

a strap member; and a clasp, having a pair of splayable fingers, each finger including at least one receiving aperture configured to receive at least a portion of the bracelet body to removably couple the strap assembly to the bracelet body, the splayable fingers being formed of a material having plastic memory;

the body including a lower and an upper section, the lower and upper sections being engageable with each other to thereby cooperatively define the cavity in the bracelet body for receiving the information-bearing medium;

the lower section including a protruding lower retention arm and the upper section including a protruding upper retention arm, the lower and upper retention arms each being sized and shaped to cooperatively form a body retention arm when the lower and upper sections are engaged with each other; and the receiving apertures of the fingers being configured to receive and secure the body retention arm to both couple the body to the strap assembly and to secure the lower and upper sections of the body in engagement with each other.

26. An information bracelet for protectively storing information related to an individual wearing the bracelet, comprising:

a bracelet body having a cavity defined therein, the cavity being configured to store and protect an information-bearing medium on which the information related to the individual can be disposed;

the body including a lower and an upper section, the lower and upper sections being engageable with each other to thereby cooperatively define the cavity in the bracelet body for receiving the information-bearing medium, the lower section including a protruding lower retention arm, and the upper section including a protruding upper retention arm, the lower and upper retention arms each being sized and shaped to cooperatively form a body retention arm when the lower and upper sections are engaged with each other; and a strap assembly, including;

a strap member; and a clasp, coupled to the strap member and removably coupled to the body retention arm, to both couple the body to the strap assembly and to secure the lower and upper sections of the body in engagement with each other.

27. The bracelet of claim 26, wherein the clasp is rotatably coupled to the body retention arm to facilitate rotation of the clasp relative to the body to allow the bracelet to conform to a shape of a wrist of the individual wearing the bracelet.

28. The bracelet of claim 26, wherein the clasp includes a pair of splayable fingers, each finger including at least one receiving aperture configured to both couple the body to the strap assembly and to secure the lower and upper sections of the body in engagement with each other.

29. The bracelet of claim 26, wherein the clasp includes a pair of splayable fingers, each formed of a material having plastic memory.

30. The bracelet of claim 26, wherein at least one of the lower and upper sections includes a seal, configured to provide a substantially water-resistant seal around at least a portion of a perimeter of the cavity.

31. The bracelet of claim 26, wherein the protruding lower retention arm includes an upper mating surface, and wherein the protruding upper retention arm includes a lower mating surface, the lower and upper mating surfaces having substantially matching contours and being configured to cooperatively form the body retention arm when the lower and upper sections are engaged with each other.

32. The bracelet of claim 31, wherein the lower and upper mating surfaces are substantially planar.

33. The bracelet of claim 32, wherein the lower retention arm and the upper retention arm each have a substantially half-circular cross section, and wherein the lower and upper retention arms cooperatively form a body retention arm having a substantially circular cross section.

34. The bracelet of claim 26, wherein the clasp includes a pair of splayable fingers, the splayable fingers defining a substantially elliptical receiving area in which the body is received by the clasp.

35. The bracelet of claim 26, wherein the information-bearing medium is substantially water resistant.

36. The bracelet of claim 26, wherein the information related to the individual includes information selected from the group consisting of: identification information; health information; medication information; scheduling information; and third party contact information.

37. A method for storing information related to an individual in a bracelet wearable by the individual, comprising the steps of:

providing a substantially water-resistant information-bearing medium on which the information related to the individual can be disposed;

storing the information-bearing medium within a cavity of the bracelet defined between a lower and an upper section of a bracelet body;

engaging the lower and upper sections with each other;

clasping a protruding portion of both the lower and upper sections with a clasp coupled to a bracelet strap; and wherein the step of clasping both the lower and upper sections includes the further step of clasping both the lower and upper protruding portions with a pair of splayable fingers, each finger including at least one receiving aperture configured to receive a portion of the lower and upper sections to removably clasp the bracelet strap to the bracelet body.

38. The method of claim 37, wherein the step of clasping both the lower and upper sections includes the further step of rotatably clasping the protruding portion of both the lower and upper sections to allow the bracelet to conform to a shape of a wrist of the individual wearing the bracelet.

39. The method of claim 37, wherein the step of clasping both the lower and upper sections includes the further step of clasping both the lower and upper protruding portions with a pair of splayable fingers formed of a material having plastic memory.

40. The method of claim 37, comprising the further step of sealing the lower and upper sections to provide a substantially water-resistant seal around at least a portion of the cavity.

41. The method of claim 37, wherein information related to the individual includes information selected from the group consisting of: identification information; health information; medication information; scheduling information; and third party contact information.

* * * * *